US007846143B1

(12) United States Patent
Abbato

(10) Patent No.: US 7,846,143 B1
(45) Date of Patent: Dec. 7, 2010

(54) PORTABLE URINAL WITH A SHAPED INLET AND A MEMBRANE VALVE

(76) Inventor: Tomasine Abbato, 1138 Greenridge La., Pittsburgh, PA (US) 15220

( * ) Notice: Subject to any disclaimer, the term of this patent is extended or adjusted under 35 U.S.C. 154(b) by 1828 days.

(21) Appl. No.: 10/705,177

(22) Filed: Nov. 10, 2003

Related U.S. Application Data

(60) Provisional application No. 60/425,921, filed on Nov. 13, 2002.

(51) Int. Cl.
*A61M 1/00* (2006.01)
*A47K 11/00* (2006.01)
*F16K 21/04* (2006.01)

(52) U.S. Cl. ........................ 604/323; 604/350; 4/144.1; 4/144.2; 4/144.3; 4/144.4; 137/512.15

(58) Field of Classification Search ....... 4/144.1-144.4; 604/323, 350; 137/512.15
See application file for complete search history.

(56) References Cited

U.S. PATENT DOCUMENTS 3,703,731 A * 11/1972 Leiser ........................ 4/144.3
3,928,875 A * 12/1975 Persson ......................... 4/451
4,059,124 A * 11/1977 Hill ............................. 137/38
4,769,215 A * 9/1988 Ehrenkranz .................. 422/58
5,010,599 A 4/1991 Nilsson
5,069,878 A * 12/1991 Ehrenkranz .................. 422/61
5,592,699 A * 1/1997 Jensen ........................ 4/144.3
5,711,037 A * 1/1998 Reichardt et al. .............. 4/301
5,785,044 A * 7/1998 Meador et al. .............. 600/573
5,797,147 A * 8/1998 Young et al. ................. 4/144.1
6,021,529 A * 2/2000 Abbato ....................... 4/144.1
6,163,892 A * 12/2000 Abbato ....................... 4/144.1
6,296,627 B1 * 10/2001 Edwards ..................... 604/347

OTHER PUBLICATIONS

Definitions of "lateral" from various online dictionaries.*
Examiner's Markup of Figures 3B and 3C of Ehrenkranz.*

* cited by examiner

*Primary Examiner*—Tatyana Zalukaeva
*Assistant Examiner*—Susan Su
(74) *Attorney, Agent, or Firm*—Eckert Seamans Cherin & Mellott, LLC; David C. Jenkins, Esquire

(57) ABSTRACT

A portable urinal that includes a container defining a liquid reservoir and a spout extending therefrom. The spout has an inlet for receiving a liquid. A valve assembly is disposed within the spout. The valve assembly has an interior region and an exterior region. The valve assembly includes a side-wall and one or more sealable openings for permitting flow of a liquid into the reservoir, while resisting undesired flow of the liquid out of the reservoir. The openings defining the line between the interior region and the exterior region. The valve assembly sidewall has a shaped contour structured to direct liquid flow into the openings.

28 Claims, 3 Drawing Sheets

PORTABLE URINAL WITH A SHAPED INLET AND A MEMBRANE VALVE

CROSS REFERENCE TO RELATED APPLICATION

This application claims priority under 35 U.S.C. §119(e) to provisional Application Ser. No. 60/425,921, filed Nov. 13, 2002, incorporated by reference.

BACKGROUND OF THE INVENTION

1. Field of the Invention

The present invention relates generally to portable urinals, and more specifically, to a portable male urinal having a valve assembly with a shaped inlet which directs urine to flow into a reservoir, and a membrane that resists backflow or spillage of the urine following use of the urinal.

2. Background Information

Portable urinals are used by those who need to urinate but cannot access a toilet, for example, patients confined to bed or pilots in light aircraft. Typically, such urinals include a urine receiving reservoir and a spout extending therefrom. The spout includes an inlet through which the urine is received and typically contains a valve structured to resist backflow.

Backflow is a long recognized problem associated with portable urinals. Backflow, or undesirable spillage, of urine may occur during use or while handling the filled portable urinal. Backflow may be caused by urine escaping the reservoir through the valve, or by urine that has entered the spout but does not pass through the valve. Backflow can result in the urine coming into contact with the person handling the portable urinal or the patient's bed in. Such backflow can cause unsanitary health conditions and result in the increased risk for further medical problems, such as infections. In addition, the workload of caretakers is increased due to the need for cleaning the patient and/or the bed following the spillage of urine thereon. Mishandling of the urinal may be a result of the bedridden patient leaving the urinal, for example, on the bed following use and then inadvertently contacting the urinal and causing spillage therefrom.

Prior art portable urinals include valves that attempt to reduce backflow. These devices, however, each have a disadvantage. For example, U.S. Pat. No. 2,358,850 provides for a male urinal having a tubular trap inserted therein and connected to the urinal container by screw threads so as to minimize leakage of liquid from the container. The tubular trap must be removed before use and then reinserted following each use. U.S. Pat. Nos. 703,131 and 4,164,795 both provide a rotating nozzle arrangement for an inlet tube which is inserted into a urine container or collector. In both patents, rotation of the nozzle elements aid resisting undesired discharge of the contents of the container or collector. Other patents, such as U.S. Pat. Nos. 6,021,529 and 6,163,892 disclose urinals having spring-biased flapper plates within a tubular valve. Such flapper valves may create a liquid gathering recess at the contact point of the flapper and the tube when the flow of liquid is insufficient to overcome the bias of the spring.

In a different type of arrangement, U.S. Pat. No. 5,592,699 discloses a non-return valve to insure that urine can only pass from the funnel area of the device into the urinal, but not back into the funnel area. The funnel area of the device, however, is configured so as to most conveniently be used in relation with a female urinal and not with a portable male urinal. In another arrangement, U.S. Pat. No. 3,499,327 discloses an upright, vertical urine collection apparatus employing a pivoted valve member for diverting a stream of urine entering the collection apparatus. The value member operates by the force and weight of the incoming stream of urine and acts to divert a first portion of the urine sample into a first receptacle while diverting a second portion into a second receptacle. This collection apparatus is not convenient for portable use, such as by a bedridden patent, and is not well suited for resisting spillage of urine contained in the collection apparatus.

Another portable urinal is shown in U.S. Pat. No. 5,010,599 that includes a valve having a generally flat plate that acts as a valve bottom which is disposed in a circular tube coupled to a reservoir. The valve bottom includes a plurality of openings. A resilient membrane is attached by a central pin to the reservoir side of the valve bottom. The resilient member is intended to flex toward the reservoir as liquid passes through the openings in the valve bottom and to seal against the openings when a liquid move backwards through the valve. This valve has at least two disadvantages. First, the valve bottom creates a generally right angle with the tube. This obstruction extends into the flow path and the corner forms a liquid gathering recess that traps liquid and prevents the liquid from passing through the openings. This fluid, which never passes through the valve, is very likely to spill out of the portable urinal. Second, the membrane tends to be very thin, and therefore, flimsy. This is required in order for the membrane to be flexible enough to allow a weak stream of liquid to cause the membrane to flex. Because the membrane is weak, the membrane may fold or curl, or simply flex under its own weight. When the membrane is flexed, the membrane does not seal against the openings, thereby allowing backflow. Even when a bead of material is provided about the perimeter of the membrane as a reinforcement, the single central attachment fails to provide a sufficient amount of support to ensure that the membrane seals the openings.

Thus, despite the various types of known portable male urinals and other urine collection devices, there remains a need for an improved portable male urinal that may be conveniently used by a patient that is confined to bed or otherwise must use a urinal. Such a portable male urinal would effectively resist backflow and undesirable spillage of urine from the urinal onto the patient or the patient's bed or both. The urinal would have a flow path from the outside to the interior of the reservoir which is free of obstructions that form liquid gathering recesses.

SUMMARY OF THE INVENTION

This need, and others, is satisfied by the present invention which provides a portable urinal that includes a container defining a liquid reservoir and a spout extending therefrom. The spout has an inlet for receiving a liquid. A valve assembly is disposed within the spout. The valve assembly has and interior region and an exterior region, a sidewall and one or more sealable openings for permitting flow of a liquid into the reservoir, while resisting undesired flow of the liquid out of the reservoir. The openings define the boundary between the interior region and the exterior region. The valve assembly sidewall has a shaped contour structured to direct liquid flow into the openings.

The valve assembly may further include a membrane in the interior region at the openings. The membrane is coupled to the sidewall by an elongated membrane support member. The membrane is flexible and flexes away from the sidewall when a liquid moves through the opening along a flow path from the outside to the reservoir. The membrane seals against the sidewall when liquid moves against the flow path. The elongated support provides sufficient support to the membrane to ensure that the membrane blocks back flow.

It is an object of this invention to provide a portable urinal that effectively resists backflow and undesirable spillage of urine from the urinal onto the patient or the patient's bed or both.

It is a further object of this invention to provide a portable urinal that resists the gathering of a liquid in a recess in an exterior region of the portable urinal.

It is a further object of this invention to provide a portable urinal having an effective valve assembly for a portable urinal which resists flow of a liquid out of the reservoir.

BRIEF DESCRIPTION OF THE DRAWINGS

A full understanding of the invention can be gained from the following description of the preferred embodiments when read in conjunction with the accompanying drawings in which.

DESCRIPTION OF THE PREFERRED EMBODIMENTS

As used herein, "interior" and "exterior" are used in relation to locations on either side of the valve assembly and/or reservoir. That is, at a location where a liquid is trapped by the valve assembly is an interior location. Whereas "inner" and "outer" are used in relation to the area enclosed by the valve assembly, spout, and/or reservoir. For example, a liquid disposed within the reservoir is both on the inner side of the reservoir and on the interior side of the valve assembly. Conversely, a liquid within the spout is on the inner side of the spout but on the exterior side of the valve assembly.

Figure 1:
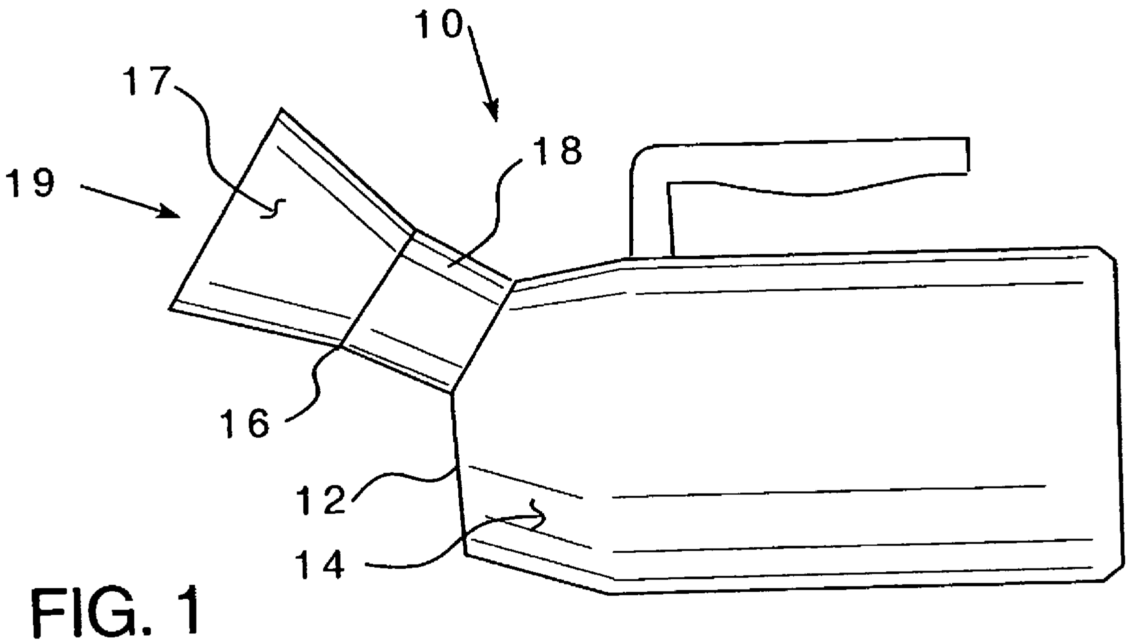
FIG. 1 is a side view of a portable urinal.
Figure 2:
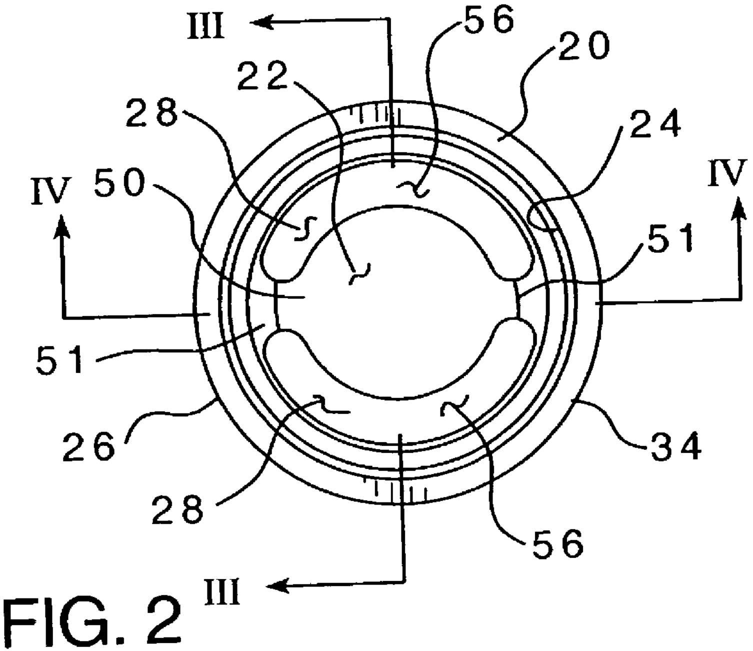
FIG. 2 is a top view of the valve assembly for the portable urinal.

As shown in FIG. 1, a portable urinal 10 includes a waterproof container 12 that defines a reservoir 14 and a spout 16. The container 12 may be either a flexible material or a rigid material. The spout 16 defines an inlet 17 that provides a means of fluid communication for a liquid to travel from the outside to the reservoir 14. Within the spout is a valve assembly 18. Thus, there is a liquid flow path 19 from the outside, through the spout 16 and valve assembly 18 into the reservoir 14. As will be described hereinafter, the valve assembly 18 includes sealable openings 28 (FIG. 2). Locations upstream of the openings are hereinafter referenced as "exterior," while locations downstream, that is, towards the reservoir 14, of the openings 28 are "interior" locations. The valve assembly 18 may be a separate structure from, or be formed integrally with, the spout 16.

As shown in FIGS. 2-5, the valve assembly 18 includes a sidewall 20 that defines a passageway 22. The sidewall 20 has an inner side 24 which is located within the passageway 22, and an outer side 26 which is located outside the passageway 22. The passageway 22 includes one or more sealable openings 28. The openings 28 define the line between an interior region 30 and an exterior region 32 of the valve assembly 18 as well as the portable urinal 10. Preferably, the valve assembly 18 is generally cylindrical.

The sidewall 20 has an outer surface 34 on the outer side 26. The sidewall outer surface 34 has a generally uniform cross-sectional shape or, where the valve assembly 18 is generally cylindrical, the sidewall 20 is annular having a generally uniform outer diameter. The sidewall 20 has an inner surface 36 on the inner side 24. The sidewall inner surface 36 is sloped in an axial direction. That is, the sidewall inner surface 36 has a first, upper diameter and a second, lower diameter. The inner surface 36 second diameter is, preferably, smaller than the first diameter and is disposed closer to the one or more openings 28 than the first diameter. The sidewall inner surface 36 terminates at the one or more openings 28. Thus, sidewall inner surface 36 has a shaped contour structured to direct liquid flow into the one or more openings 28. In a preferred embodiment, the sidewall inner surface 36 is curved from the upper diameter to the lower diameter. Thus, unlike the prior art, there is not a perpendicular barrier extending from the sidewall 20 into the liquid flow path 19 forming a liquid gathering recess. Additionally, because the sidewall outer surface 34 is generally uniform and the sidewall inner surface 36 has a smaller diameter adjacent to the openings, the sidewall 20 grows thicker closer to the openings 28.

Figure 3:
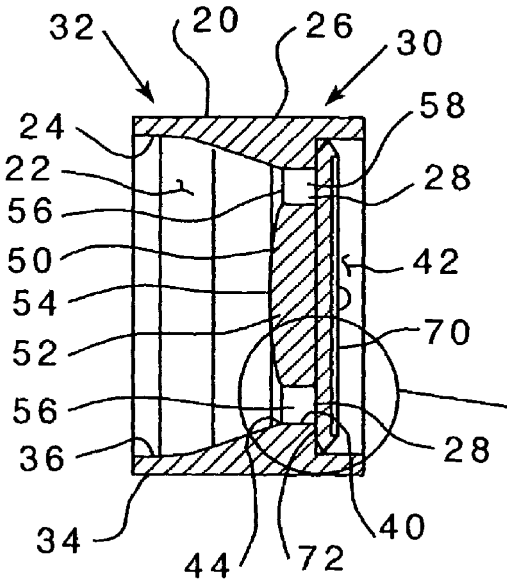
FIG. 3 is a cross-sectional view of the valve assembly for the portable urinal.
Figure 3A:
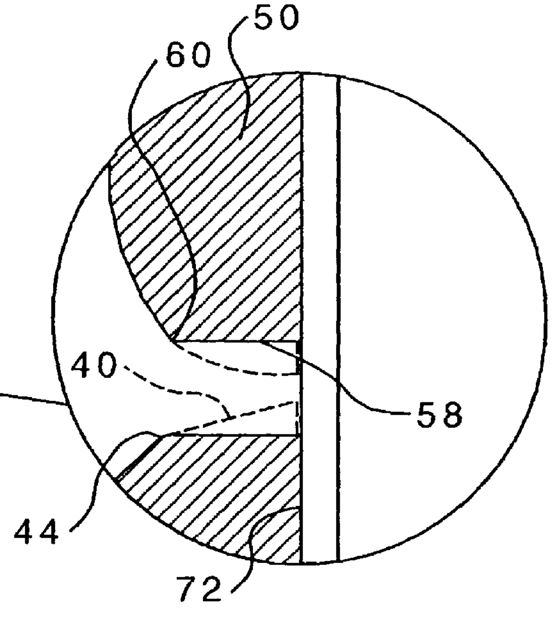
Figure 4:
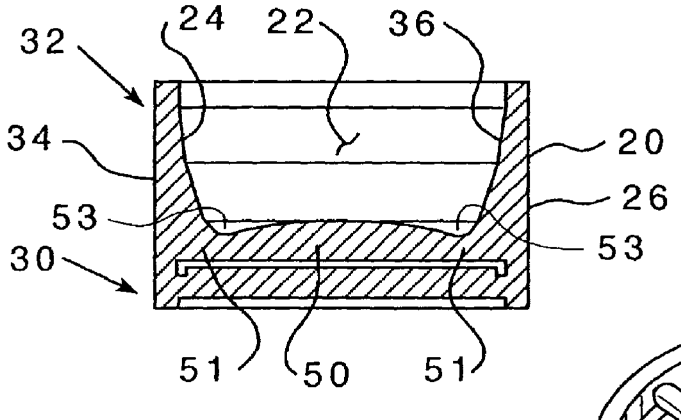
FIG. 4 is another cross-sectional view of the valve assembly for the portable urinal.
Figure 5:
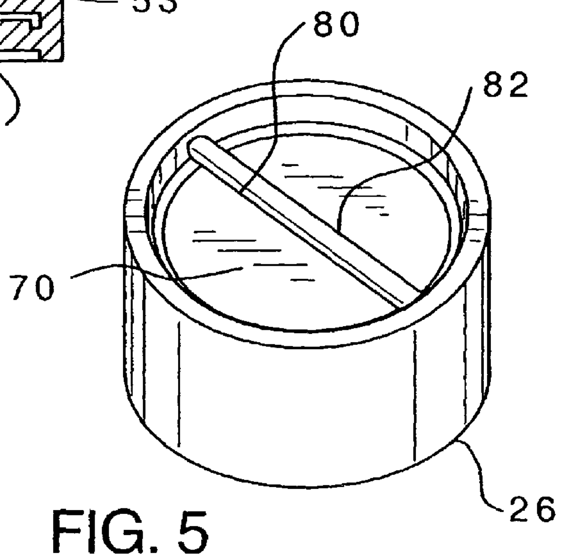
FIG. 5 is an isometric view of the interior side of the valve assembly.

The one or more openings 28 each include an axially extending sidewall 40. The axially extending sidewall 40 has, preferably, a uniform diameter. However, as shown in FIG. 3A, the axially extending sidewall 40 may be sloped, that is, have a reducing diameter in the direction of the flow path 19. In the preferred embodiment, the sidewall inner surface 36 defines a central opening 42. The central opening has a diameter that is generally the same as the inner surface 36 second diameter. Between the central opening 42 and the inner surface 36 second diameter is a first transition region 44. The first transition region 44 has a convex, rounded profile. This shape ensures that a liquid is more likely to flow through the central opening 42 than stop on a sharp edge.

In a preferred embodiment, a lateral member 50 is disposed in the central opening 42. The lateral member 50 is integrally coupled to the sidewall inner surface 36. The lateral member 50 extends across the central opening 42 and is coupled to opposite sides of the sidewall inner surface 36. The lateral member 50 is coupled to the sidewall inner surface 36 by two fillet regions 51. The lateral member 50 further includes an integral central disk 52. The lateral member 50 and central disk 52 share an exterior surface 54. The exterior surface 54 is generally convex and protrudes into the valve assembly exterior region 32. That is, the exterior surface 54 is arched away from the interior region 32. Additionally, the fillet regions 51 also include generally convex exterior surfaces 53. The central disk 52 has a diameter that is smaller than the diameter of the central opening 42. Thus, with the central disk 52 disposed within the central opening 42, at least two peripheral openings 56 are created. The convex exterior surface 54 of the central disk 52 may be shaped so that the exterior surface 54 extends to the interior surface of the central disk 52, as shown in FIG. 3A. In the preferred embodiment shown in FIG. 3, however, the central disk 52 includes a radial surface 58 that extends in an axial direction and which has a generally uniform diameter. The radial surface 58 extends generally parallel to the axially extending sidewall 40. Between the exterior surface 54 and the radial surface 58 is a second transition region 60 having a generally rounded profile. As with the first transition region 44, the second transition region 60 ensures that a liquid is more likely to flow through the two peripheral openings 56 instead of stopping on a sharp edge.

The valve assembly 18 further includes a membrane 70. The membrane 70 is a thin, flexible material such as, but not limited to, latex rubber. The membrane 70 is coupled to the interior side of the central disk 52. The membrane 70 has a diameter sufficient to extend across the peripheral openings 56. As noted hereinbefore, the sidewall 20 is thickest adjacent to the peripheral openings 56. At a point just beyond the peripheral openings 56, that is, within the interior region 30, the sidewall inner surface 36 is larger than the sidewall inner surface 36 second diameter. That is, on the interior side of the peripheral openings 56, there is a flange 72. The flange 72 is, generally, perpendicular to the sidewall inner surface 36 and, as such, forms a liquid gathering recess for a fluid moving in a direction opposite of the flow path 19. In the preferred embodiment, the membrane is sized to contact the flange 72.

Figure 6:
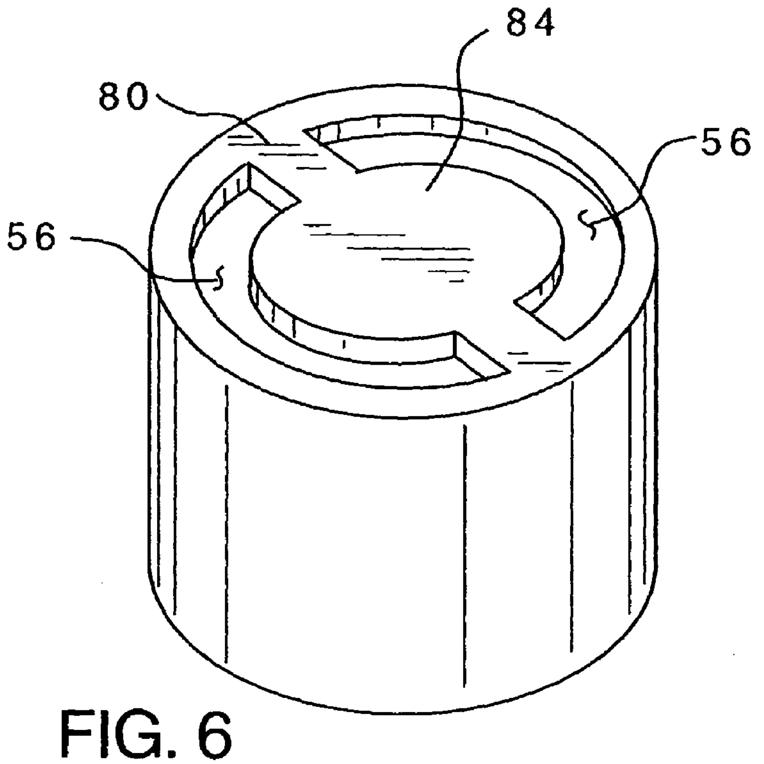
FIG. 6 is an isometric view of an alternate embodiment of the membrane support member for the portable urinal.

The membrane 70 is coupled to the lateral member 50 by a membrane support member 80. The membrane support member 80 extends across the central opening 42 and, preferably, in direction generally parallel to the lateral member 50. As such, the membrane support member 80 provides support to the membrane 70 along the entire diameter. This support causes the membrane 70 to create an effective seal against the flange 72. The membrane support member 80 may be a slender rod 82, as shown best in FIG. 5, or may include disk shaped portion 84, as shown in FIG. 6. The disk shaped portion 84 may have a diameter up to, but no larger than, the central disk 52. The disk shaped portion 84 provides support to the entire perimeter of the membrane 70. The diameter of the disk shaped portion 84 may be adjusted based on the resiliency of the membrane 70 so that the membrane 70 is not overly rigid. That is, the membrane 70 must be sufficiently flexible to allow liquid to pass from the exterior region 32 into the interior region 30 as the liquid moves in the direction of the flow path 19.

Figure 7:
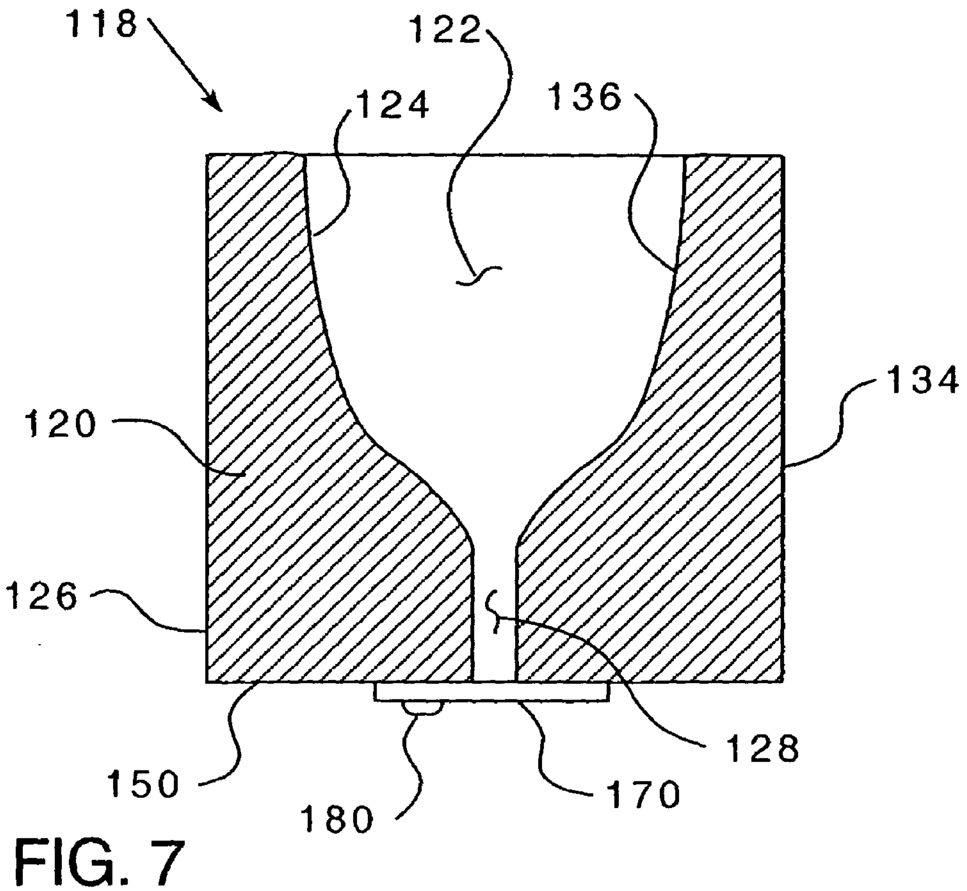
FIG. 7 is a cross-sectional view of an alternate embodiment of the valve assembly for the portable urinal.

An alternate embodiment of the valve assembly 118 is shown in FIG. 7. The alternate valve assembly 118 may be disposed in the spout 16 of the portable urinal 10. In this embodiment the alternate valve assembly 118 does not include two peripheral openings or a bridge member. Similar to the first embodiment, the alternate valve assembly 118 includes a sidewall 120 that defines a passageway 122. The sidewall 120 has an inner side 124 which is located within the passageway 122, and an outer side 126 which is located outside the passageway 122. The passageway 122 includes a sealable opening 128. The opening 128 defines a boundary between an interior region 130 and an exterior region 132 of the valve assembly 118. Preferably, the valve assembly 118 is generally cylindrical. The sidewall 120 has an outer surface 134 on the outer side 126. The sidewall outer surface 134 has a generally uniform cross-sectional shape or, where the alternate valve assembly 118 is cylindrical, the sidewall 120 has a generally uniform outer diameter. The sidewall 120 has an inner surface 136 on the inner side 124. The sidewall inner surface 136 is curved in an axial direction. That is, the sidewall inner surface 136 has a first, upper diameter and a second, lower diameter. The inner surface 136 second diameter is, preferably, smaller than the first diameter and is disposed closer to the opening 128 than the first diameter. The sidewall inner surface 136 terminates at the opening 128. Thus, sidewall inner surface 136 has a shaped contour structured to direct liquid flow into the opening 128. That is, unlike the prior art, there is not a perpendicular container extending into a liquid flow path 119 and forming a liquid gathering recess. The interior side of the valve assembly 118 forms a generally planar surface 150.

The alternate valve assembly 118 also includes a membrane 170. The membrane 170 is coupled to the planar surface 150 adjacent to the opening 128. The means of coupling the membrane 170 to the planar surface 150 is an elongated membrane support member 180. The membrane support member 180 is disposed adjacent to the opening 128 and, as such, provides more support that the prior art single mounting point.

While specific embodiments of the invention have been described in detail, it will be appreciated by those skilled in the art that various modifications and alternatives to those details could be developed in light of the overall teachings of the disclosure. For example, the central disk 52 may be supported by an X-shaped lateral member (not shown) and include an X-shaped membrane support member. Accordingly, the particular arrangements disclosed are meant to be illustrative only and not limiting as to the scope of invention which is to be given the full breadth of the claims appended and any and all equivalents thereof.

What is claimed is:

1. A portable urinal comprising:

a container defining a liquid reservoir and a spout extending therefrom;

said spout having an inlet for receiving a liquid;

a valve assembly disposed within said spout, said valve assembly having a sidewall and one or more sealable openings for permitting flow of a liquid into said reservoir, while resisting undesired flow of the liquid out of said reservoir, said valve assembly further having an interior region and an exterior region, said openings defining the line between said interior region and said exterior region;

said valve assembly sidewall having a shaped contour structured to direct liquid flow into said openings and wherein there is no barrier extending perpendicular to said sidewall into the flow path of said liquid;

said valve assembly sidewall is structured to resist the gathering of a liquid in a recess in an exterior region of the portable urinal;

said valve assembly sidewall has one or more generally parallel, outer surfaces and one or more generally sloped inner surfaces; and said one or more inner surfaces slope toward, and terminate adjacent, said one or more openings;

said valve assembly sidewall is an annular sidewall having a generally circular outer surface with an outer diameter and one inner surface having a first, upper diameter and a second, lower diameter, said inner surface curving from said upper diameter to said lower diameter; and said valve assembly sidewall further defining a central opening.

2. The portable urinal of claim 1 wherein said inner surface first diameter is larger than said inner surface second diameter.

3. The portable urinal of claim 2 wherein, said central opening has an axially extending sidewall with a generally uniform diameter, said central opening diameter being generally the same as said inner surface second diameter; and said valve assembly sidewall includes a transition region between said curved inner surface and said axial sidewall, said transition region having a rounded profile.

4. The portable urinal of claim 3 wherein, said valve assembly includes a lateral member;

said lateral member being integral to said sidewall and extending across said central opening and having a central disk;

said central disk having diameter smaller than said central opening diameter, thereby dividing said central opening into two or more peripheral openings.

5. The portable urinal of claim 4 wherein said central disk includes a exterior surface, said exterior surface being convex and extending into said exterior region.

6. The portable urinal of claim 5 wherein, said central disk includes a radial surface extending generally parallel to said axial sidewall; and said central disk includes a second transition region between said exterior surface and said radial surface, said second transition region having a rounded profile.

7. The portable urinal of claim 6 wherein, said valve assembly includes a membrane, said membrane coupled to said lateral member and disposed on the interior side of said valve assembly; and said membrane extending across said two or more peripheral openings.

8. The portable urinal of claim 7 wherein, said valve assembly sidewall includes an interior portion located in said valve assembly interior region and an exterior portion located in said valve assembly exterior region;

said valve assembly sidewall outer surface extends across both said interior portion and exterior portion;

said valve assembly sidewall inner surface disposed on said exterior portion;

said valve assembly sidewall further having a interior, inner surface disposed on said interior portion;

said interior, inner surface having a diameter larger than said surface second diameter, thereby forming a sidewall flange at the interior region edge of said one or more openings and forming a liquid gathering recess.

9. The portable urinal of claim 8 wherein, said membrane is sized to contact said flange.

10. The portable urinal of claim 9 wherein, said valve assembly includes a membrane support member, said membrane support member extending across said central opening, said membrane being disposed between said lateral member and said membrane support member.

11. The portable urinal of claim 10 wherein, said membrane support member extends adjacent and generally parallel to said lateral member.

12. The portable urinal of claim 2 wherein, said central opening has an axially extending sidewall having a first, exterior diameter and a second, interior diameter, said central opening first, exterior diameter being generally the same as said inner surface second diameter and said central opening second, interior diameter being smaller than said central opening first, exterior diameter; and said valve assembly sidewall includes a transition region between said curved inner surface and said axial sidewall, said transition region having a rounded profile.

13. A portable urinal comprising:

a container defining a liquid reservoir and a spout extending therefrom;

said spout having an inlet for receiving a liquid;

a valve assembly disposed within said spout, said valve assembly having a sidewall and one or more sealable openings for permitting flow of a liquid into said reservoir, while resisting undesired flow of the liquid out of said reservoir, said valve assembly further having an interior region and an exterior region, said openings defining the line between said interior region and said exterior region;

said valve assembly sidewall having a shaped contour structured to direct liquid flow into said openings and wherein there is no barrier extending perpendicular to said sidewall into the flow path of said liquid;

said valve assembly sidewall is an annular sidewall having a generally circular outer surface with an outer diameter and one inner surface having a first, upper diameter and a second, lower diameter, said inner surface curving from said upper diameter to said lower diameter;

said valve assembly sidewall further defining a central opening having a diameter;

said valve assembly includes a lateral member;

said lateral member being integral to said sidewall and extending across said central opening and having a central disk;

said central disk having diameter smaller than said central opening diameter, thereby dividing said central opening into two or more peripheral openings.

14. The portable urinal of claim 13 wherein, said central disk includes an exterior surface, said exterior surface being generally convex and extending into said exterior region.

15. The portable urinal of claim 14 wherein, said central disk includes a radial surface extending generally parallel to said axial sidewall; and said central disk includes a second transition region between said exterior surface and said radial surface, said second transition region having a rounded profile.

16. The portable urinal of claim 15 wherein, said valve assembly includes a membrane, said membrane coupled to said lateral member and disposed on the interior side of said valve assembly; and said membrane extending across said two or more peripheral openings.

17. The portable urinal of claim 16 wherein, said valve assembly sidewall includes an interior portion located in said valve assembly interior region and an exterior portion located in said valve assembly exterior region;

said valve assembly sidewall outer surface extends across both said interior portion and exterior portion;

said valve assembly sidewall inner surface disposed on said exterior portion;

said valve assembly sidewall further having a interior, inner surface disposed on said interior portion; and said interior, inner surface having a diameter larger than said surface second diameter, thereby forming a sidewall flange at the interior region edge of said one or more openings and forming a liquid gathering recess.

18. The portable urinal of claim 17 wherein, said membrane is sized to contact said flange.

19. The portable urinal of claim 18 wherein, said valve assembly includes a membrane support member, said membrane support member extending across said central opening, said membrane being disposed between said lateral member and said membrane support member.

20. The portable urinal of claim 19 wherein, said membrane support member extends adjacent and generally parallel to said lateral member.

21. A valve assembly for a portable urinal comprising:

a sidewall defining a passageway and having an interior region and an exterior region;

one or more sealable openings within said passageway for permitting flow of a liquid through said passageway, while resisting undesired backflow of the liquid through said passageway, said openings defining the boundary between said interior region and said exterior region; and said sidewall having a shaped contour structured to direct liquid flow into said openings and wherein there is no barrier extending perpendicular to said sidewall into the flow path of said liquid;

said sidewall resists the gathering of a liquid in a recess in said exterior region;

said sidewall has one or more generally parallel, outer surfaces and one or more generally curved inner surfaces; and said one or more inner surfaces curve toward, and terminate at, said one or more openings;

said sidewall generally defines a circular tube having one, circular outer surface with an outer diameter and one inner surface having a first, upper diameter and a second, lower diameter, said inner surface curving from said upper diameter to said lower diameter; and said sidewall further defining a central opening;

said inner surface first diameter is larger than said inner surface second diameter;

said central opening has an axially extending sidewall with a generally uniform diameter, said central opening diameter being generally the same as said inner surface second diameter;

said sidewall includes a transition region between said curved inner surface and said axial sidewall, said transition region having a rounded profile;

a lateral member;

said lateral member being integral to said sidewall and extending across said central opening and having a central disk; and said central disk having diameter smaller than said central opening diameter, thereby dividing said central opening into two or more peripheral openings.

22. The valve assembly of claim 21 wherein, said central disk includes an exterior surface, said exterior surface being generally convex and extending into said exterior region.

23. The valve assembly of claim 22 wherein, said central disk includes a radial surface extending generally parallel to said axial sidewall; and said central disk includes a second transition region between said exterior surface and said radial surface, said second transition region having a rounded profile.

24. The valve assembly of claim 23 wherein, said valve assembly further includes:

a membrane, said membrane coupled to said lateral member and disposed on the interior side of said valve assembly; and said membrane extending across said two or more peripheral openings.

25. The valve assembly of claim 24 wherein, said sidewall includes an interior portion located in said interior region and an exterior portion located in said exterior region;

said sidewall outer surface extend across both said interior portion and exterior portion;

said sidewall inner surface disposed on said exterior portion;

said sidewall further having a interior, inner surface disposed on said interior portion; and said interior, inner surface having a diameter larger than said surface second diameter, thereby forming a sidewall flange at the interior region edge of said one or more openings and forming a liquid gathering recess.

26. The valve assembly of claim 25 wherein, said membrane is sized to contact said flange.

27. The valve assembly of claim 26 wherein, said valve assembly further includes a membrane support member, said membrane support member extending across said central opening, said membrane being disposed between said lateral member and said membrane support member.

28. The valve assembly of claim 27 wherein, said membrane support member extends adjacent and parallel to said bridge-lateral member.

* * * * *

UNITED STATES PATENT AND TRADEMARK OFFICE

CERTIFICATE OF CORRECTION

PATENT NO. : 7,846,143 B1
APPLICATION NO. : 10/705177
DATED : December 7, 2010
INVENTOR(S) : Tomasine Abbato It is certified that error appears in the above-identified patent and that said Letters Patent is hereby corrected as shown below:

Front page, second column, under ABSTRACT, line 8, "defining" should read --define--.
Column 1, line 33, "bed in." should read --bed.--.
Column 1, line 49, "U.S. Pat. Nos. 703,131" should read --U.S. Pat. Nos. 3,703,731--.
Column 1, line 52, "aid resisting" should read --aid in resisting--.
Column 2, line 2, "value" should read --valve--.
Column 2, line 7, "patent" should read --patient--.
Column 2, line 17, "liquid move" should read --liquid moves--.
Column 2, line 53, "has and" should read --has an--.
Column 6, line 5, "that" should read --than--.
Column 7, line 5, "a exterior" should read --an exterior--.
Column 7, line 28, "a interior" should read --an interior--.
Column 8, line 44, "a interior" should read --an interior--.
Column 10, line 18, "surface extend" should read --surface extends--.

Signed and Sealed this
Thirteenth Day of December, 2011

David J. Kappos
*Director of the United States Patent and Trademark Office*